(12) United States Patent
Tamura et al.

(10) Patent No.: US 11,007,454 B2
(45) Date of Patent: May 18, 2021

(54) DISTILLATION APPARATUS FOR NMP

(71) Applicant: MITSUBISHI CHEMICAL ENGINEERING CORPORATION, Chuo-ku (JP)

(72) Inventors: Takahiro Tamura, Chuo-ku (JP); Hisataka Takeda, Chuo-ku (JP); Kaori Kudou, Kurashiki (JP)

(73) Assignee: MITSUBISHI CHEMICAL ENGINEERING CORPORATION, Chuo-ku (JP)

( * ) Notice: Subject to any disclaimer, the term of this patent is extended or adjusted under 35 U.S.C. 154(b) by 0 days.

(21) Appl. No.: 16/498,969

(22) PCT Filed: Mar. 30, 2017

(86) PCT No.: PCT/JP2017/013282
§ 371 (c)(1),
(2) Date: Sep. 27, 2019

(87) PCT Pub. No.: WO2018/179239
PCT Pub. Date: Oct. 4, 2018

(65) Prior Publication Data
US 2020/0155961 A1 May 21, 2020

(51) Int. Cl.
*B01D 3/42* (2006.01)
*C07D 207/267* (2006.01)

(52) U.S. Cl.
CPC ....... *B01D 3/4261* (2013.01); *C07D 207/267* (2013.01)

(58) Field of Classification Search
CPC .......... B01D 3/00; B01D 3/42; B01D 3/4261; C07D 207/267
See application file for complete search history.

(56) References Cited

U.S. PATENT DOCUMENTS

2012/0241307 A1 9/2012 Miyata et al.
2015/0367249 A1 12/2015 Miyata et al.

FOREIGN PATENT DOCUMENTS

| EP | 2 479 167 A1 | 7/2012 |
| JP | 8-109167 A | 4/1996 |
| WO | WO 2012/120666 A1 | 9/2012 |

OTHER PUBLICATIONS

Google machine translation of WO 2012/120666 published Sep. 13, 2012.*

(Continued)

*Primary Examiner* — Brian A McCaig
(74) *Attorney, Agent, or Firm* — Oblon, McClelland, Maier & Neustadt, L.L.P.

(57) ABSTRACT

A distillation apparatus is capable of regenerating spent NMP from an on-site process for lithium ion battery electrodes. The distillation apparatus has a raw material tank, a side-cut distillation column, and a product tank. The distillation column has a top portion where a liquid to be treated is separated into a high-concentration NMP and water containing light-boiling components, a bottom portion where refluxed liquid in the distillation column is further distilled to separate the refluxed liquid into a high-purity NMP and the high-concentration NMP containing high-boiling components, and a mid-stage portion from which the high-purity NMP is withdrawn as side-cut vapor. The distillation column has, at a rear stage, a condenser for condensing the high-purity NMP withdrawn as the side-cut vapor, and a flow controller for regulating an amount of a liquid of the high-purity NMP withdrawn from the condenser to the product tank.

20 Claims, 3 Drawing Sheets

(56) References Cited

OTHER PUBLICATIONS

Extended European Search Report dated Jan. 13, 2020 in Patent Application No. 17903364.2, 6 pages.
International Search Report dated Jun. 13, 2017 in PCT/JP2017/013282, 2 pages.
International Preliminary Report on Patentability and Written Opinion dated Oct. 10, 2019 in PCT/JP2017/013282 (with English Translation), 13 pages.

* cited by examiner (a)

(b)

SECTION A-A

DISTILLATION APPARATUS FOR NMP

TECHNICAL FIELD

The present invention relates to a distillation apparatus for NMP, and more particularly, to a distillation apparatus for NMP which is capable of purifying a spent NMP (N-methyl-2-pyrrolidone) recovered from a process for production of an electrode for lithium ion secondary batteries, etc., on-site for recycling the NMP.

BACKGROUND ART

Upon production of lithium ion secondary batteries, a base material in the form of a metal foil is coated with an electrode material comprising an active substance such as a lithium compound, a binder such as polyvinylidene fluoride, and N-methyl-2-pyrrolidone (hereinafter referred to merely as "NMP") as a solvent, and the resulting coated material is calcined to produce an electrode. Conventionally, the NMP generated in a gaseous state in the calcination step has been recovered by an adsorption method utilizing activated carbon or zeolite, or a water-absorbing method. The thus recovered NMP has been then transported to chemical plants by a tank lorry, etc. Thereafter, in the chemical plants, the recovered NMP is purified by conventionally known distillation methods to obtain a purified NMP having a purity of not less than 99.9% by weight, similarly to initial production of the NMP.

On the other hand, from the standpoint of reducing recycling cost, i.e., transport cost and treatment cost required in chemical plants for loading and unloading of the NMP in a tank and pretreatments for control of a concentration of the NMP, etc., the present inventors have previously proposed a distillation apparatus for NMP which is capable of purifying the NMP on-site. The distillation apparatus is equipped with a single tower-type distillation column, and is designed to reduce its size by reducing the number of equipments attached thereto, such as a boiling reboiler, a cooling condenser, a pump and other metering devices. The distillation column used in the distillation apparatus is a side-cut type distillation column which is constructed such that water comprising light-boiling components is removed from a raw NMP in a top portion thereof to separate a high-concentration NMP from the raw NMP, and high-boiling components are further removed from the high-concentration NMP in a bottom portion of the distillation column to obtain a purified high-purity NMP which can be then withdrawn as a side-cut liquid from a mid-stage portion of the distillation column. By using such a distillation column, it is possible to obtain the high-purity NMP having a purity of not less than 99.9% by weight at a recovery rate of about 85%. Furthermore, the distillation apparatus is additionally provided, as an automatic treatment function, with a start-up function for initiating a continuous treatment operation in which a reduced pressure operation and a circulation operation are sequentially performed for controlling the distillation column in a stationary state upon initiating the continuous treatment operation of the distillation apparatus; and an operational mode switching function in which upon conducting the continuous treatment operation, an operational mode of the distillation apparatus is switched again to the circulation operation according to a liquid level in a raw material tank or a product tank. With the provision of the automatic treatment function, the distillation apparatus can be operated in a simple and safe manner corresponding to the variation of throughput or water content in the raw material (refer to Patent Literature 1).

CITATION LIST

Patent Literature

Patent Literature 1: International Patent Application Laid-Open (PCT Pamphlet) No. WO 2012/120666

SUMMARY OF INVENTION

Technical Problem

By the way, in the distillation apparatus in which the NMP is purified on-site, it is important not only to purify the NMP into a high-purity NMP, but also to further enhance a recovery rate of the NMP. An object of the present invention is to provide a distillation apparatus for NMP which is capable of regenerating a spent NMP recovered from a process for production of an electrode for lithium ion secondary batteries on-site, in which the NMP can be purified in a simple and safe manner irrespective of variation in concentration of water in the raw material or throughput, and a recovery rate of the NMP can be further enhanced.

Solution to Problem

In the present invention, in order to contemplate reduction in size of the distillation apparatus, there is adopted a single tower-type distillation column of a side-cut type in which water comprising light-boiling components is removed from a raw NMP at a top portion of the distillation column to separate a high-concentration NMP from the raw NMP; high-boiling components are further removed from the high concentration NMP at a bottom portion of the distillation column; and a high-purity NMP in a vaporized state which comprises a less amount of impurities is withdrawn as a side-cut vapor from a mid-stage portion of the distillation column and then liquefied by a condenser to thereby further enhance a recovery rate of the high-purity NMP. Furthermore, in the present invention, by regulating an amount of the high-purity NMP withdrawn from the condenser to a product tank by a flow control means to control an amount of the high-purity NMP condensed in the condenser according to variation in amount of the side-cut vapor withdrawn, it is possible to maintain a height of a liquid level in the bottom portion of the distillation column in a predetermined range and realize stable operation of the distillation column.

That is, in an aspect of the present invention, there is provided a distillation apparatus for NMP in which a spent NMP comprising light-boiling components and high-boiling components as impurities is purified, said distillation apparatus comprising a raw material tank for storing the spent NMP as a liquid to be treated, a distillation column in which the liquid to be treated which is supplied from the raw material tank is subjected to distillation to obtain a purified high-purity NMP, and a product tank for storing the high-purity NMP obtained in the distillation column, in which:

the distillation column is a side-cut type distillation column that comprises a top portion in which the liquid to be treated is separated into a high-concentration NMP having a concentration of not less than 99% by weight and water comprising the light-boiling components, a bottom portion in which the liquid to be treated is separated into the high-purity NMP having a concentration of not less than 99.9% by weight and the high-concentration NMP comprising the high-boiling components, and a mid-stage portion from which the high-purity NMP is withdrawn as a side-cut vapor; and the distillation column is further provided at a rear stage thereof, with a condenser for condensing the high-purity NMP withdrawn as the side-cut vapor, and a flow control means for regulating an amount of a liquid of the high-purity NMP withdrawn from the condenser to the product tank on the basis of a height of a liquid level in the bottom portion of the distillation column.

Advantageous Effects of Invention

In the distillation apparatus for NMP according to the present invention, water comprising light-boiling components is removed from the raw NMP at a top portion of the distillation column to separate a high-concentration NMP therefrom, whereas high-boiling components are further removed from the NMP at a bottom portion of the distillation column to separate and obtain a purified high-purity NMP, and further the high-purity NMP is withdrawn as a side-cut vapor from a mid-stage portion of the distillation column and then liquefied by a condenser, so that it is possible to further enhance a recovery rate of the high-purity NMP. Furthermore, in the distillation apparatus of the present invention, the amount of a liquid of the high-purity NMP withdrawn from the condenser can be regulated by a flow control means on the basis of a height of a liquid level in the bottom portion of the distillation column, so that the height of the liquid level in the bottom portion of the distillation column can be maintained in a predetermined range. As a result, it is possible to conduct stable operation of the distillation apparatus irrespective of variation in throughput or content of water in the raw material.

BRIEF DESCRIPTION OF DRAWINGS

FIG. 2 is a partial view showing a construction of a mid-stage portion of a distillation column in the distillation apparatus of FIG. 1, in which FIG. 2(a) is a vertical section of the mid-stage portion of the distillation column, and FIG. 2(b) is a horizontal section of the mid-stage portion of the distillation column.

DESCRIPTION OF EMBODIMENTS

An embodiment of the distillation apparatus for NMP according to the present invention (hereinafter also referred to merely as a "distillation apparatus") is described below. The "NMP" as used in the present invention means N-methyl-2-pyrrolidone or an aqueous solution comprising N-methyl-2-pyrrolidone as a main component. In addition, examples of impurities contained in the spent NMP as a liquid to be treated (hereinafter also referred to merely as a "raw NMP") include light-boiling components whose boiling point lies between respective boiling points of water and NMP, such as formic acid, and high-boiling components derived from NMP, such as γ-butyl lactone (GBL) and n-methyl succinimide.

Figure 1:
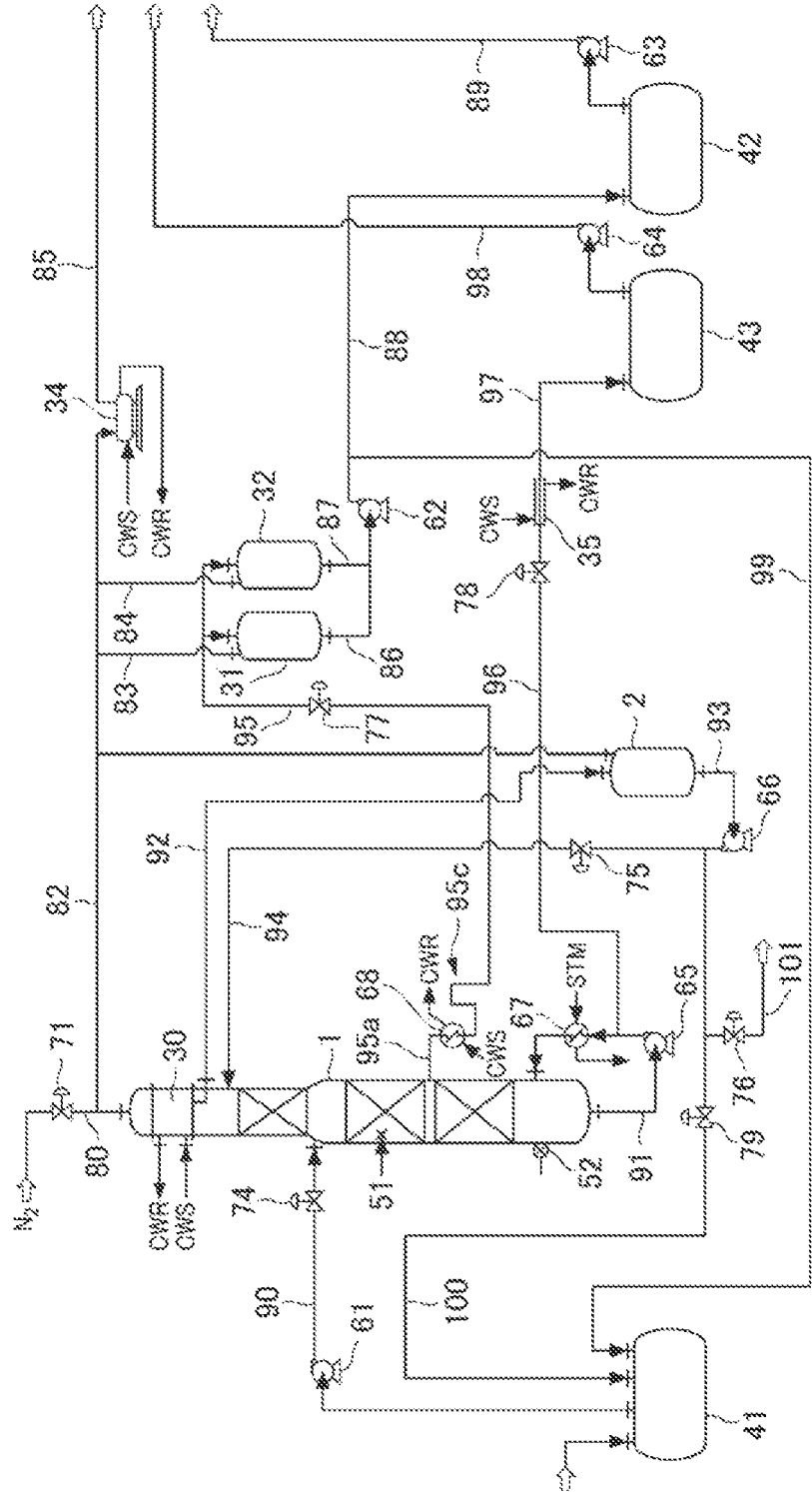
FIG. 1 is a flow diagram showing an example of a construction of a main portion of a distillation apparatus for NMP according to the present invention.

The distillation apparatus according to the present invention is an automatically operable single tower type distillation apparatus for purifying the raw NMP comprising the light-boiling components and the high-boiling components as impurities. As shown in FIG. 1, the distillation apparatus according to the present invention generally comprises a raw material tank 41 for storing the raw NMP as a liquid to be treated, a distillation column 1 of a side-cut type in which the liquid to be treated which is supplied from the raw material tank is subjected to distillation to purify the raw NMP and thereby obtain a high-purity NMP; a first check drum 31 and a second check drum 32 in which the high-purity NMP obtained from the distillation column is temporarily recovered to obtain a test specimen for analysis; a product tank 42 for storing the high-purity NMP recovered in these check drums as a product; and a waste liquid tank 43 for storing the high-concentration NMP (waste liquid) comprising the high-boiling components which are recovered from the bottom portion of the distillation column 1.

The raw material tank 41 is a container for storing the raw NMP having, for example, a concentration of not more than 95% by weight, usually a concentration of about 70% by weight to about 90% by weight which is discharged, for example, from a process for production of an electrode for lithium ion secondary batteries, and may be provided for conducting the distillation treatment in a continuous and efficient manner. Connected to the raw material tank 41 are not only a flow path for delivering the raw NMP from the process for production of an electrode to the raw material tank, but also a raw material feed flow path 90 for feeding the raw NMP as the liquid to be treated to the distillation column 1. In the figures, the reference numeral 61 denotes a raw material feed pump, and the reference numeral 74 denotes a flow control valve.

The distillation column 1 is a distillation column of a side-cut type in which the raw NMP fed is subjected distillative purification. The distillation column is constituted of a top portion in which the raw NMP is separated into the high-concentration NMP having a concentration of not less than 99% by weight and water comprising the light-boiling components, a bottom portion in which the raw NMP is separated into the high-purity NMP having a concentration of not less than 99.9% by weight and the high-concentration NMP comprising the high-boiling components, and a mid-stage portion from which the high-purity NMP is withdrawn as a side-cut vapor. The distillation column 1 may be a conventionally known distillation column, namely, a distillation column that is constituted of a packing column in which irregular packing materials or regular packing materials are packed, a plate column in which a number of trays (plates) for gas-liquid contact such as porous plate trays are disposed, etc.

The distillation column 1 is constructed such that the raw NMP to be treated is supplied to an upper portion of the mid-stage portion of the distillation column through the above flow path 90. The distillation column 1 is equipped at the bottom portion thereof with a boiling mechanism comprising a reboiler 67 for heating and vaporizing the raw NMP. Such a boiling mechanism serves as a mechanism for boiling the raw NMP in the bottom portion of the distillation column 1, and comprises the reboiler 67 for heating and vaporizing the raw NMP by heat exchange with a heat medium such as water vapor, a flow path 91 for circulation of the bottom liquid through which the raw NMP is withdrawn from the bottom portion of the distillation column and fed to the reboiler 67 and the NMP vaporized in the reboiler is returned back to the bottom portion of the distillation column, and a waste liquid withdrawal pump 65.

As the reboiler 67, there may be used a multi-pipe type heat exchanger in which a number of flow paths are constructed by a plurality of heat transfer pipes. On an upstream side of the reboiler 67 in the flow path 91, there is provided a flow path 96 which is branched from the flow path 91 for feeding a part of the bottom liquid circulated in the bottom portion of the distillation column 1, i.e., for feeding the high-concentration NMP concentrated in the distillation column 1 as the waste liquid to the waste liquid tank 43. The aforementioned high-concentration NMP is discharged from the the bottom portion of the distillation column for the purpose of preventing concentration of peroxides.

The distillation column 1 is also provided at the top portion thereof with a condenser 30 for condensing the vapor separated from the raw NMP. As the condenser 30, there may be usually used those condensers of a multi-pipe type, a spiral type, a plate type, a double tube type, etc., in which a cooling medium is flowed through a plurality of heat transfer pipes or heat transfer plates constituting a number of flow paths, and a condensable vapor (vapor separated by distillation) is passed therethrough for liquefying the condensable vapor. The condenser 30 is provided at a bottom thereof with a flow path 92 through which condensed water comprising the light-boiling components as impurities is discharged as a distillate out of the system. The flow path 92 serves as a flow path for feeding the condensed water comprising the light-boiling components to a drain tank 2.

The drain tank 2 is connected to a flow path 93, a pump 66 and a flow path 94 for returning the distillate fed from the distillation column 1 and temporarily stored in the drain tank back to an upper stage portion of the distillation column 1. Further, branched from the flow path 94 is a flow path 100 for feeding the distillate stored in the drain tank 2 back to the raw material tank 41 upon conducting the below-mentioned circulation operation of the distillation apparatus. In addition, branched from the aforementioned flow path 100 is a flow path 101 for discharging the distillate stored in the drain tank 2 out of the system upon conducting the continuous operation of the distillation apparatus. Incidentally, the distillation column 1 is connected at the top thereof with the below-mentioned flow path 80 for reducing a pressure within the distillation column 1 and feeding an inert gas thereto.

On the flow path for circulating the bottom liquid in the aforementioned boiling mechanism, there is provided a flow path 96 which is branched therefrom for feeding a part of the high-concentration NMP circulated in the bottom portion of the distillation column 1, i.e., for withdrawing the bottom liquid comprising the high-boiling components as impurities, as the bottoms thereof. On a downstream side of the flow path 96, there are disposed a waste liquid cooler 35 for cooling the thus withdrawn high-concentration NMP, a flow path 97 for delivering the thus cooled high-concentration NMP to a waste liquid tank 43, and a flow path 98 for appropriately withdrawing the high-concentration NMP as a waste liquid temporarily stored in the waste liquid tank 43 out of the system. Meanwhile, the reference numeral 78 denotes a flow control valve for controlling a flow rate of the bottom liquid, and the reference numeral 64 denotes a pump for discharging the waste liquid.

In the present invention, the high-purity NMP in a vaporized state which comprises a less amount of impurities is withdrawn to enhance a recovery rate of the NMP. For this reason, in the distillation apparatus of the present invention, there is used the distillation column 1 of a side-cut type which is constructed such that the high-purity NMP is withdrawn as a side-cut vapor from the mid-stage portion thereof. The distillation column 1 is provided at a rear stage thereof (at a downstream side thereof), with a condenser 68 for condensing the high-purity NMP withdrawn as the side-cut vapor.

Figure 2:
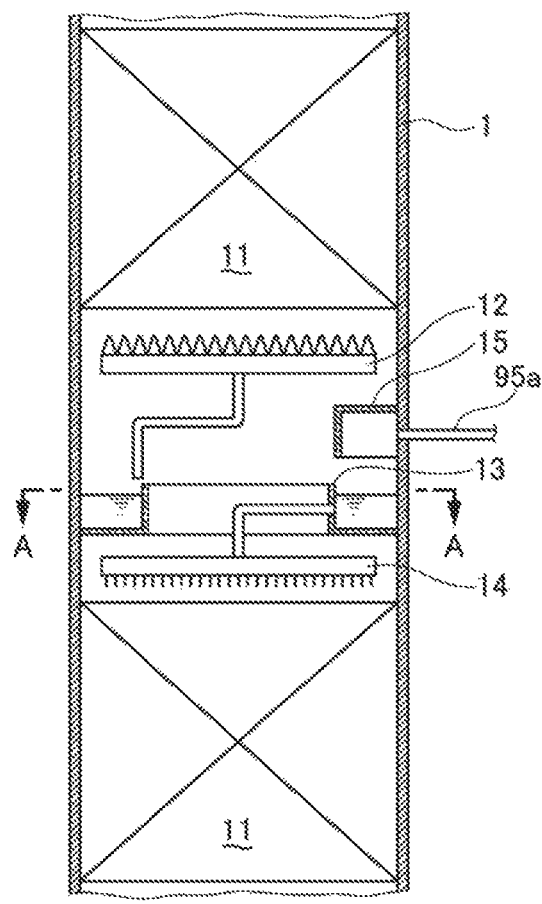
Figure 2:
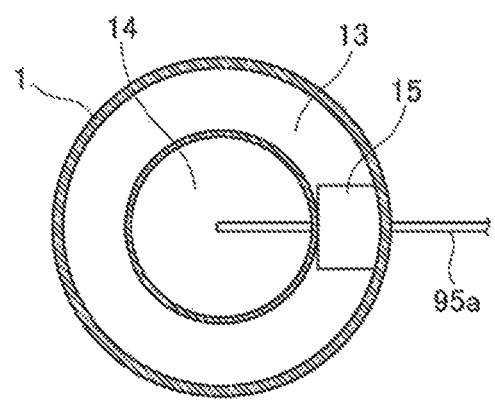

As shown in FIG. 2, in the mid-stage portion of the distillation column 1, there are provided a collector 12 for collecting the high-concentration NMP that is separated from the raw NMP in the top portion of the distillation column, a weir 13 for storing the high-concentration NMP in a liquid state which has been collected by the collector, and a distributor 14 for feeding the high-concentration NMP retained by the weir as a refluxed liquid to the bottom portion of the distillation column. The reference numeral 11 denotes packed materials respectively serving for stabilizing the distillation operation. In the present invention, in order to further subject the refluxed liquid to distillation treatment at the bottom portion of the distillation column and withdraw the resulting high-purity NMP in the form of a vapor, a flow path 95a for withdrawal of the side-cut vapor which extends to the condenser 68 is connected to the mid-stage portion of the distillation column 1, and an inner circumferential portion of the distillation column 1 is equipped with a liquid guard cover 15 of an open-bottomed box shape at a connecting position thereof to the flow path 95a for withdrawal of the side-cut vapor in order to prevent the other liquid from entering into the the high-concentration NMP. The liquid guard cover 15 is a cover member of a generally rectangular box shape whose bottom surface or one side surface is opened, and may be disposed, for example, above the aforementioned weir 13.

Figure 3:
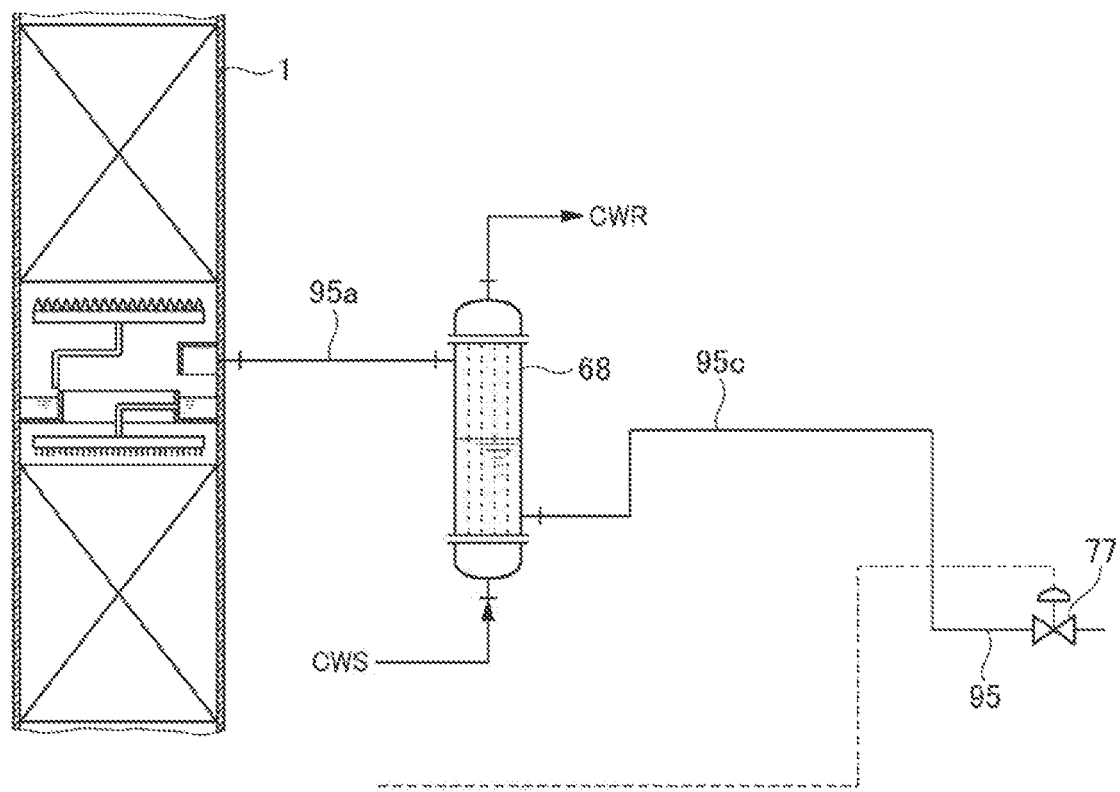
FIG. 3 is a flow diagram showing a condenser and a flow control means for regulating an amount of a liquid withdrawn in the distillation apparatus of FIG. 1.

As shown in FIG. 3, the condenser 68 used in the present invention is capable of not only condensing the high-purity NMP obtained in the form of vapor, but also storing a predetermined amount of the liquefied high-purity NMP therein. As the condenser 68, there may be used such a condenser in which a cooling medium is flowed through a plurality of heat transfer pipes or heat transfer plates constituting a number of flow paths, and a condensable vapor (vapor of the high-purity NMP) as a material to be treated is passed therethrough for liquefaction of the condensable vapor similarly to the top portion of the distillation column 1, but a multi-pipe type condenser may be usually used for buffering variation of the liquid level.

Furthermore, in the distillation apparatus, the variation of the raw material, in other words, the variation of throughput or content of water in the raw material (variation of a concentration of NMP therein) tends to cause variation of an amount of the high-purity NMP withdrawn as the side-cut vapor. In the present invention, in order to stably conduct the distillation operation, on a flow path 95 extending on a rear stage (on a downstream side) of the condenser 68, there is provided a flow control means for regulating an amount of a liquid of the high-purity NMP withdrawn from the condenser 68 to the product tank 42 on the basis of a height of a liquid level in the bottom portion of the distillation column 1. More specifically, the flow control means is usually constructed of a flow control valve 77, and is operated such that the height of the liquid level in the bottom portion of the distillation column 1 is maintained in a predetermined range by controlling a flow rate of the liquid flowing therethrough using such a flow control valve. In other words, the flow control valve 77 is capable of detecting signals of a level gauge 52 attached to the bottom portion of the distillation column 1, and an opening degree of the flow control valve 77 is controlled such that the height of the liquid level in the bottom portion of the distillation column 1 is maintained at a generally constant value by cascade control using the below-mentioned control device. As a result, it is possible to exhibit the function of controlling the amount of the high-purity NMP condensed by the condenser 68 according to variation of the amount of the side-cut vapor withdrawn from the distillation column 1.

Moreover, as shown in FIG. 3, in the condenser 68, the vapor is introduced into an upper portion of a container of the condenser via the flow path 95a, and the high-purity NMP in a liquid state is withdrawn from a lower portion of the container thereof via the flow path 95. In order to stabilize the liquid level in the condenser 68 and supercool the high-purity NMP delivered from the condenser 68, a part of the flow path 95 on a downstream side of the condenser 68 is formed into a raise-up portion 95c. The flow path 95 through which the liquefied high-purity NMP is withdrawn is connected to the first check drum 31 and the second check drum 32.

The above first check drum 31 and second check drum 32 are provided for analyzing a purity of the high-purity NMP obtained from the distillation column 1 and judging whether or not the high-purity NMP is acceptable as a final product. Although not shown in FIG. 1, a changeover valve may be disposed on the flow path 95 between the first check drum 31 and the second check drum 32 for alternately receiving the high-purity NMP in the first check drum 31 and the second check drum 32, respectively.

Meanwhile, the distillation column 1 is connected at a top thereof with the below-mentioned flow path 82 for reducing a pressure within the distillation column and feeding an inert gas to the distillation column. In addition, the first check drum 31 and the second check drum 32 are connected with the below-mentioned flow paths 83 and 84, respectively, for reducing a pressure within the respective containers and feeding an inert gas thereto.

Also, in order to withdraw the purified high-purity NMP, the first check drum 31 is connected with a flow path 86, and the second check drum 32 is connected with a flow path 87. These flow paths 86 and 87 are connected to the product tank 42 through a product withdrawal pump 62 and a flow path 88. Although not shown in the figures, the flow path 86 and the flow path 87 are respectively provided thereon with a switching valve for delivering the high-purity NMP from either one of the first check drum 31 and the second check drum 32 to the product tank 42 in a switching manner. In addition, there is provided a flow path 99 which is branched from the flow path 88 and serves for feeding the high-purity NMP withdrawn from the mid-stage portion of the distillation column 1 and stored in either one of the first check drum 31 and the second check drum 32 back to the raw material tank 41 upon conducting the below-mentioned circulation operation. The product tank 42 is a container for storing the high-purity NMP and may be constructed such that the high-purity NMP is fed, for example, to a battery production process through a product feed pump 63 and a flow path 89, if necessary.

In the distillation apparatus according to the present invention, in order to conduct the distillation operation under reduced pressure similarly to an ordinary distillation operation, there may also be additionally provided a reduced pressure line for evacuating an inside of the system. In addition, in order to prevent inclusion of oxygen and control a pressure within the system, there may also be additionally provided an inert gas line for feeding an inert gas such as nitrogen gas into the system.

More specifically, the distillation column 1 is connected at a top thereof with a flow path 80 which extends from a nitrogen gas feed facility and is provided thereon with a pressure regulating valve 71. A flow path 82 is also connected to the flow path 80. The above flow paths 83 and 84 are branched from the flow path 82 and connected to the first check drum 31 and the second check drum 32, respectively. Furthermore, the flow path 82 is coupled at a tip end thereof to a vacuum pump 34 for evaluating an inside of the system. A flow path 85 is a flow path for evacuation by the vacuum pump 34.

In the distillation apparatus according to the present invention, in order to control the distillation operation in the distillation column 1 to thereby control a height of the liquid level in the bottom portion of the distillation column 1 to a predetermined range, the distillation column 1 is provided, for example, in a packing layer formed in the mid-stage portion thereof, with a thermometer 51, and further the distillation column 1 is provided at a bottom portion thereof, with the aforementioned level gauge 52. Using a control device loaded with a distillation program, operation of the boiling mechanism, opening and closing of the respective flow paths, switching therebetween, flow rate control therethrough, etc., are controlled on the basis of preset treatment conditions as well as detection signals from detectors by which the aforementioned temperatures, the liquid level, etc., are detected.

Furthermore, in the preferred embodiment of the present invention, the distillation apparatus is further constructed so as to execute an automatic treatment function to be accomplished by the above control device. Examples of the automatic treatment function include a start-up function in which a reduced pressure operation and a circulation operation are sequentially performed to control the distillation column in a stationary state, and then a continuous treatment operation of the distillation apparatus is initiated, an operational mode switching function in which an operational mode of the distillation apparatus is switched from the continuous treatment operation to the circulation operation, and an automatic stopping function. In the following, the method for operating the distillation apparatus according to the present invention by the side-cut vapor withdrawal method and the method for purifying the NMP using the distillation apparatus are explained merely as an embodiment thereof.

Reduced Pressure Operation

By manipulating a control panel for initiating an operation of the distillation apparatus, first, in order to perform the reduced pressure operation, the vacuum pump 34 is actuated to reduce an inside pressure of each of the distillation column 1, the first check drum 31 and the second check drum 32 to a predetermined value through the flow paths 80, 82, 83 and 84. In this case, the inside pressure of the system is once evacuated, for example, until reaching 100 torr or less, and then a trace amount of nitrogen gas is fed from the nitrogen gas feed facility to the distillation column 1, the first check drum 31 and the second check drum 32 through the flow path 80 to maintain the pressures within these devices at a constant value. Upon the above reduced pressure operation, in order to prevent production of by-products owing to increase in inside temperatures of the respective devices, for example, the pressure within the distillation column 1 is set to 100 torr, and the pressures the first check drum 31 and the second check drum 32 are also set to 100 torr, by controlling the pressure regulating valve 71.

Circulation Operation

After conducting the reduced pressure operation, it should be avoided to immediately perform a distillation treatment, and a total reflux operation using a make-up solution previously stored in the distillation column 1 is performed to stabilize the conditions within the system. With the total reflux operation, the distillation column 1 is controlled in a stationary state, so that the operation of the distillation apparatus can be smoothly transferred to the next continuous treatment operation. Meanwhile, by controlling the reflux ratio in the distillation apparatus to set the recovery rate of the high-purity NMP to about 90%, it is possible to obtain the high-purity NMP having a purity of not less than 99.9% by weight.

More specifically, first, steam is supplied to the reboiler 67 of the distillation column 1 to actuate the boiling mechanism and thereby initiate heating of the distillation column. The flow rate of the steam is gradually increased until reaching such a flow rate as designed, for example, over about 40 min. In this case, if the change in temperature between the packing layer formed in the top portion of the distillation column 1 and the packing layer formed in the bottom portion of the distillation column 1 is not so large, when it is attempted to control the boiling mechanism on the basis of the temperatures detected at the bottom and top portions of the distillation column, the followability of the operation of the boiling mechanism tends to be poor, so that it is not possible to maintain a constant concentration of water in the liquid in the mid-stage portion of the distillation column.

In consequence, in the circulation operation, the temperature of the packing layer formed in the mid-stage portion of the distillation column which is likely to suffer from the temperature change is detected by the thermometer 51 to perform a cascade control for suitably controlling the flow rate of the steam in the reboiler 67. By performing such a cascade control, the temperature of the packing layer formed in the mid-stage portion of the distillation column can be maintained, for example, in a temperature range of 120 to 130° C., so that it is possible to control a concentration of water in the side-cut vapor withdrawn from the mid-stage portion of the distillation column. Thus, it is possible to conduct optimum heating of the distillation column 1 corresponding to the variation in amount of the raw NMP fed to the distillation column 1 and the variation in concentration of the raw NMP, in other words, the variation in content of water in the raw NMP. As a result, the operation of the distillation apparatus is able to cope with occurrence of remarkable change in composition of the raw NMP, and further both of the concentration of water in the NMP in the side-cut portion and the concentration of the NMP in water in the top portion of the distillation column can be reduced, resulting in enhanced separation efficiency. That is, in the present invention, when the circulation operation (total reflux operation) is performed to keep the distillation column in a stationary state, the flow rate of the steam through the reboiler in the distillation column 1 may be controlled such that the temperature detected by the thermometer 51 is equal to a temperature corresponding to the boiling point of NMP.

Successively, while operating the distillation column 1, the circulation operation in which the raw NMP is continuously fed thereto, and the distillate from the top portion of the distillation column 1 as well as the side-cut vapor from the mid-stage portion of the distillation column 1 are fed back to the raw material tank 41 is performed, thereby finely adjusting preset values of data for the automatic operation. As a result, it is possible to control operating conditions within the system to optimum ones.

More specifically, first, continuous feed of the raw NMP is initiated. Upon feeding the raw NMP, the opening degree of the flow control valve 74 is gradually increased, for example, the flow rate of the raw NMP is increased to the value as designed over 90 min, so as not to cause turbulence of the operation owing to rapid feed of the raw NMP to the distillation column 1. On the other hand, continuous discharge of the distillate from the distillation column 1 is initiated. At this time, the opening degree of the flow control valve 75 is gradually increased so as to reach a predetermined flow rate over about 15 min, so that turbulence of the operation within the distillation column owing to rapid variation in reflux ratio therethrough can be prevented. The reflux ratio of the distillation column 1 is controlled by operation of a reflux distribution mechanism. More specifically, the water comprising the light-boiling components which is discharged from the top portion of the distillation column 1 and stored in the drain intermediate tank 2 is entirely refluxed to the top portion of the distillation column through the flow path 94 by using the pump 66 and controlling the opening degree of the flow control valve 75. Thereafter, in order to stabilize the conditions within the system, the distillate from the top portion of the distillation column which is then stored in the drain intermediate tank 2 is fed back to the raw material tank 41 through the flow path 100 by controlling the opening degree of the flow control valve 79, whereby it is possible to control the amount of the liquid refluxed to the top portion of the distillation column 1.

Next, continuous withdrawal of the side-cut vapor from the mid-stage portion of the distillation column 1 is initiated, and the thus withdrawn side-cut vapor is liquefied in the condenser 68. At this time, the opening degree of the flow control valve 77 is gradually increased to reach the predetermined flow rate over about 15 min, whereby turbulence within the distillation column owing to rapid change in amount of the side-cut vapor withdrawn can be suppressed. Then, the liquid level in the bottom portion of the distillation column 1 is detected by the level gauge 52 to adjust the opening degree of the flow control valve 77, whereby the height of the liquid level in the bottom portion of the distillation column 1 is controlled to a predetermined range. In this case, when the liquid level in the bottom portion of the distillation column exceeds the upper limit of a reference height thereof, the opening degree of the flow control valve 77 is increased to increase the amount of the liquid withdrawn from the condenser 68 and thereby increase the amount of the liquid condensed in the condenser 68. On the other hand, when the liquid level in the bottom portion of the distillation column is less than the lower limit of the reference height thereof, the opening degree of the flow control valve 77 is reduced to reduce the amount of the liquid withdrawn from the condenser 68 and thereby reduce the amount of the liquid condensed in the condenser 68, so that the liquid level in the bottom portion of the distillation column can be well controlled.

The high-purity NMP liquefied in the condenser 68 is fed through the flow path 95 and received in the first check drum 31 and the second check drum 32. The resulting high-purity NMP is fed back to the raw material tank 41 from the first check drum 31 and the second check drum 32 through the flow paths 86 and 87 and the flow path 99 in order to maintain a constant concentration of the NMP in the raw material as well as allow constant distribution of the concentration of the NMP within the system. In addition, discharge of the bottom liquid from the bottom portion of the distillation column 1 is initiated. At this time, the flow control valve 78 is subjected to ratio control on the basis of the flow rate of the liquid fed to the distillation column 1, and the bottom liquid in an amount of about 10% by weight of the flow rate of the liquid fed is withdrawn through the flow path 96 as a waste liquid for suppressing concentration of peroxides therein.

As described above, the operation conditions of the distillation apparatus are controlled to optimum conditions by performing the circulation operation. Then, the place to which the high-purity NMP obtained from the mid-stage portion of the distillation column 1 is to be fed is switched from the raw material tank 41, for example, to the product tank 42, thereby initiating the continuous treatment operation. More specifically, the distillation apparatus according to the present invention is provided, as an automatic treatment function, with a start-up function of previously performing a circulation operation in the distillation column 1 in which the raw NMP in the raw material tank 41 (liquid to be treated) is fed to the distillation column 1 and the distillate from the tip portion of the distillation column 1 and the high-purity NMP obtained from the mid-stage portion of the distillation column 1 are fed back to the raw material tank 41 to control the distillation column in a stationary state, and then initiating a continuous treatment operation of the distillation apparatus. With such a start-up function, it is possible to control the conditions within the system in a stationary state so as to completely adapt them to the variation in amount of the raw NMP fed and composition of the raw NMP, thereby enabling smooth transfer to the continuous treatment operation.

Continuous Treatment Operation

In the continuous treatment operation, the distillate from the top portion of the distillation column 1 (water comprising the light-boiling components) is discharged out of the system through a flow path 92 and the drain intermediate tank 2, and the high-purity NMP obtained from the distillation column 1 is fed to the first check drum 31 and the second check drum 32 through a flow path 95 and temporarily stored therein, and the bottom liquid in the bottom portion of the distillation column 1 (high-concentration NMP comprising the high-boiling components) is fed to a water liquid tank 43 through a flow path 96, a waste liquid cooler 35 and a flow path 97.

The high-purity NMP that is withdrawn as the side-cut vapor from the mid-stage portion of the distillation column 1 and then liquefied in the condenser 68 is alternately fed to and stored in the first check drum 31 and the second check drum 32 in a switching manner. At this time, the switching between the first check drum 31 and the second check drum 32 is automatically conducted by controlling a change-over valve (not shown) disposed on the flow path 95 between these check drums on the basis of the value detected by a level gauge (not shown) disposed in each of the first check drum 31 and the second check drum 32.

For example, when a predetermined amount (for example, an amount corresponding to 80% by weight of a capacity of the container) of the high-purity NMP is stored in the first check drum 31, feeding of the high-purity NMP through the flow path 95 is switched so as to feed the high-purity NMP to the second check drum 32, and a switching valve (not shown) disposed on the flow path 86 is opened, and a product withdrawal pump 62 is actuated to conduct a minimum flow operation such that the concentration of the NMP in the first check drum 31 becomes uniform. Then, before the second check drum 32 is fulfilled, the purity of the high-purity NMP (product) in the first check drum 31 is analyzed. When the purity of the high-purity NMP meets the standard as required, the high-purity NMP is delivered to the product tank 42 through the flow path 88. Similarly, when a predetermined amount of the high-purity NMP is stored in the second check drum 32, the switching of feed of the high-purity NMP to the first check valve 31 through the flow path 95 is conducted, and a switching valve (not shown) disposed on the flow path 87 is opened, and the product withdrawal pump 62 is actuated to conduct a minimum flow operation such that the concentration of the NMP in the second check drum 32 becomes uniform. Then, before the first check drum 31 is fulfilled, the purity of the high-purity NMP (product) in the second check drum 32 is analyzed. When the purity of the high-purity NMP meets the standard as required, the high-purity NMP is delivered to the product tank 42.

Meanwhile, the purity of the high-purity NMP is analyzed by sampling a part of the high-purity NMP from the respective check drums 31 and 32 through a sampling flow path (not shown) and subjecting the thus sampled NMP to gas chromatography. In addition, in the case where the purity of the NMP does not meet the predetermined standard, the NMP stored in the respective check drums 31 and 32 is returned to the raw material tank 41 through the flow path 99. On the other hand, the waste liquid (high-concentration NMP comprising the high-boiling components) stored in the waste liquid tank 43 is appropriately discharged to drums or a lorry car out of the system through a waste liquid discharge pump 64 and a flow path 98.

Switching of Operation

In the continuous treatment operation, there may also occur such a case in which the throughput or content of water in the raw NMP vary depending upon the variation in process for production of an electrode, so that the amount of the raw NMP stored in the raw material tank 41 or the amount of the product stored in the product tank 42 (amount of the high-purity NMP stored) also vary. In consequence, when the amount of the raw NMP stored in the raw material tank 41 is reduced during the continuous treatment operation or when the amount of the high-purity NMP stored in the product tank 42 is increased during the continuous treatment operation, the operation of the distillation apparatus is not stopped but kept in a stand-by state, and transferred again to the above circulation operation.

More specifically, the distillation apparatus according to the present invention is also provided, as an automatic treatment function, with an operational mode switching function in which upon the continuous treatment operation, an operational mode of the distillation apparatus is switched again to the circulation operation in the case where the height of the liquid level in the raw material tank 41 is lowered up to a predetermined height during the continuous treatment operation or in the case where the height of the liquid level in the product tank 42 is raised up to a predetermined height during the continuous treatment operation. The height of the liquid level in the raw material tank 41 (lower limit height) is preset, for example, to a height corresponding to 20% by weight of a capacity of the raw material tank, and the height of the liquid level in the product tank 42 (upper limit height) is preset, for example, to a height corresponding to 90% by weight of a capacity of the product tank.

Furthermore, the aforementioned operational mode switching function may be conducted such that the operation is switched by detecting the height of the liquid level in each of the first check drum 31 and the second check drum 32.

That is, in the preferred embodiment, not only in the case where the height of the liquid level in the raw material tank 41 is lowered up to a predetermined height during the continuous treatment operation or in the case where the height of the liquid level in the product tank 42 is raised up to a predetermined height during the continuous treatment operation as described above, but also in the case where the height of the liquid level in the first check drum 31 or the second check drum 32 is raised up to a predetermined height during the continuous treatment operation, the operation is switched again to the circulation operation.

Thus, after transferring to the circulation operation during the continuous treatment operation, the operation conditions of the distillation column 1 can be automatically adjusted as described above. Then, it is judged whether or not the height of the liquid level in each of the raw material tank 41, the product tank 42, the first check drum 31 and the second check drum 32 fall within an allowable range. When the height of the liquid level lies within the allowable range, the operation of the distillation apparatus is transferred again to the automatic continuous treatment operation. In the present invention, with the above operational mode switching function, it is possible to operate the distillation apparatus in a suitable manner adaptable to the variation in throughput of the raw material NMP or the variation in content of water in the raw material NMP, and obtain a purified high-purity NMP in a safe and stable manner.

Stopping of Operation

During the continuous treatment operation as described above, in the case where the control panel is manipulated for stopping the operation or in the case where an interlock mechanism is actuated owing to detection of any failure (in the case of emergent stopping), the operation of the distillation apparatus is automatically stopped according to the following procedure on the basis of a preset program. That is, upon stopping the operation of the distillation apparatus, first, the feeding of steam to the reboiler 67 of the boiling mechanism in the distillation column 1 is stopped, whereby the withdrawal of each of the distillate, side-cut vapor and bottom liquid in the distillation column 1 is stopped. Next, after stopping all of the pumps including the raw material feed pump 61, the product withdrawal pump 62 and the vacuum pump 34, vacuum breaking operation is carried out, whereby an inside pressure of the system is increased by feeding nitrogen thereto until reaching approximately an atmospheric pressure.

More specifically, the distillation apparatus according to the present invention is provided, as an automatic treatment function, with an automatic stopping function in which in response to the operation for stopping operation of the distillation apparatus or the emergent stopping operation, the operation of the reboiler in the distillation column, the feeding of the liquid to be treated from the raw material tank, and the withdrawal of the distillate, side-cut vapor and bottom liquid from the distillation column are stopped, and an inert gas is fed to the distillation column 1 to thereby equalize the pressure within the distillation column. In the present invention, with the provision of the automatic stopping function as described above, it is possible to maintain the composition of the liquid within the distillation column 1 in the same state as upon stopping the operation, and more smoothly start again the operation without turbulence of the composition of the liquid being present within the distillation column.

As described above, in the distillation apparatus according to the present invention, the water comprising the light-boiling components is removed from the top portion of the distillation column 1 to purify the NMP and thereby obtain the high-concentration NMP, the high-boiling components are removed from the high-concentration NMP from the bottom portion of the distillation column 1, and the high-purity NMP in a vaporized state which comprises a less amount of impurities is withdrawn as the side-cut vapor from the mid-stage portion of the distillation column 1 and then liquefied in the condenser 68, whereby it is possible to increase a recovery rate of the NMP to not less than 90%. Furthermore, the amount of the high-purity NMP withdrawn from the condenser 68 is controlled by the flow control valve 77 as the flow control means on the basis of the height of the liquid level in the bottom portion of the distillation column 1, so that the height of the liquid level in the bottom portion of the distillation column 1 can be maintained within a predetermined range. In consequence, the distillation apparatus can be stably operated irrespective of variation in throughput or content of water in the raw material.

Moreover, the distillation apparatus according to the present invention is provided, as an automatic treatment function, with a start-up function in which a reduced pressure operation and a circulation operation are successively performed in the distillation column 1 to control the distillation column in a stationary state, and then a continuous treatment operation of the distillation apparatus is initiated; and an operational mode switching function in which upon the continuous treatment operation, the height of the liquid level in each of the raw material tank 41 and the product tank 42 is detected, and the operation of the distillation apparatus is switched to the circulation operation in response to the variation in amount of the raw NMP fed or the content of water in the raw NMP. Therefore, it is possible to purify the NMP on-site in a simple and safe manner by automatically operating the distillation apparatus without need of highly skilled techniques.

Meanwhile, in the distillation apparatus according to the present invention, the raw material tank 41, the product tank 42, the waste liquid tank 43 and equipments attached thereto may be conventionally known ones except for the distillation column 1 and equipments attached thereto. In addition, in the present invention, a ceramic membrane unit having an acid resistance is disposed on the flow path for feeding the raw NMP discharged, for example, from the process for production of an electrode to the raw material tank 41, or on the flow path 90 for feeding the raw NMP from the raw material tank 41 to the distillation column 1, to subject the raw NMP to dehydration treatment using the ceramic membrane, so that a load applied to the distillation column 1 can be reduced. That is, in the case where water is previously removed from the raw NMP using the ceramic membrane, it is possible to considerably reduce energy costs required for boiling and cooling the distillate, and it is also possible to purify the NMP into a still higher-purity NMP.

EXAMPLES

Example

Using the distillation apparatus shown in FIGS. 1 to 3, the aforementioned distillation operation was carried out to perform simulation in which a spent NMP used as the raw material was purified to obtain a high-purity NMP. In the simulation, a distillation column having a capacity of about 50 cm$^3$ was installed as the distillation column 1, and a multi-pipe type condenser having a heat transfer surface area of about 35 m² was disposed as the condenser 68. With such a distillation apparatus, a side-cut vapor was withdrawn from the distillation column 1 and liquefied in the condenser 68 to recover the NMP having a purity of 99.9% and determine a recovery rate of the NMP.

The spent NMP as the raw material had an NMP concentration of 80.0% by weight, an $H_2O$ concentration of 20.0% by weight and an HE concentration of 500 to 600 ppm. The raw material (spent NMP) was fed from the raw material tank 41 to the distillation column 1 at a feed rate of 1500 kg/hr to purify the NMP by continuous operation thereof. As a result, it was confirmed that the high-purity NMP having an NMP concentration of 99.9% by weight and an $H_2O$ concentration of 100 ppm was obtained at a recovery rate of 90%.

Comparative Example

The same distillation operation as described hereinbefore was carried out by the method of withdrawing the side-cut liquid from the distillation column 1, in which the same simulation of purifying the spent NMP as the raw material to obtain a high-purity NMP was conducted. The purification for obtaining the high-purity NMP was carried out under the same conditions as used in the aforementioned Example except that a simplified cooler was used in place of the condenser 68 for the purpose of cooling the side-cut liquid. As a result, it was confirmed that the high-purity NMP having the composition similar to that of Example, i.e., having an NMP concentration of 99.9% by weight and an $H_2O$ concentration of 100 ppm was obtained at a recovery rate of 85%.

INDUSTRIAL APPLICABILITY

The distillation apparatus for NMP according to the present invention is capable of purifying the NMP on-site in a simple and safe manner without need of high skilled technologies irrespective of variation in concentration of water in a raw material or throughput, and therefore can be suitably used for regenerating a spent NMP recovered from a process for production of an electrode for lithium secondary batteries, etc.

REFERENCE SIGNS LIST

1: Distillation column;
11: Packing material;
12: Collector;
13: Weir;
14: Distributor;
15: Liquid guard cover;
2: Drain intermediate tank;
30: Condenser;
31: First check drum;
32: Second check drum;
34: Vacuum pump;
35: Waste liquid cooler;
41: Raw material tank;
42: Product tank;
43: Waste liquid tank;
51: Thermometer;
52: Level gauge;
61: Raw material feed pump;
62: Product withdrawal pump;
63: Product feed pump;
64: Waste liquid discharge pump;
65: Waste liquid withdrawal pump;
66: Drain withdrawal pump;
67: Reboiler;
68: Condenser;
71: Pressure regulating valves;
74 to 79: Flow control valves;
80 to 101: Flow paths;
95c: Raise-up portion.

The invention claimed is:

1. A distillation apparatus configured for NMP distillation such that a spent NMP comprising light-boiling components and high-boiling components as impurities is purified, the apparatus comprising:
   a raw material tank configured to store spent NMP as a liquid to be treated;
   a distillation column configured such that liquid to be treated, which is supplied from the raw material tank, is subjected to distillation to obtain a purified high-purity NMP; and
   a product tank configured to store the high-purity NMP obtained in the distillation column,
   wherein the distillation column is a side-cut distillation column comprising:
   a top portion configured such that the liquid to be treated is separated into a high-concentration NMP having a concentration of not less than 99% by weight and water comprising light-boiling components;
   a bottom portion configured such that the liquid to be treated is separated into the high-purity NMP having a concentration of not less than 99.9% by weight and the high-concentration NMP comprising high-boiling components;
   a mid-stage portion configured such that the high-purity NMP is withdrawn as a side-cut vapor;
   a condenser, at a rear stage of the distillation column, configured to condense the high-purity NMP withdrawn as a side-cut vapor;
   a flow controller configured to regulate an amount of a liquid of the high-purity NMP withdrawn from the condenser to the product tank on the basis of a height of a liquid level in the bottom portion of the distillation column; and
   a flow path configured to withdraw the side-cut vapor which extends up to the condenser and is connected to the mid-stage portion of the distillation column,
   wherein an inner circumferential portion of the distillation column comprises a liquid guard cover of an open-bottomed box shape at a connecting position thereof to the flow path for withdrawing the side-cut vapor, and
   wherein the liquid guard cover is configured to prevent liquid from entering into the flow path.

2. The apparatus of claim 1, wherein the flow controller is a flow control valve configured to control and maintain the height of the liquid level in the bottom portion of the distillation column in a predetermined range.

3. The apparatus of claim 1, configured to carry out an automatic treatment function comprising:
   a start-up function in which after previously performing a reduced pressure operation of the distillation column, a circulation operation in which the liquid to be treated is fed from the raw material tank to the distillation column, and the distillate and the side-cut vapor solution in the distillation column are fed back to the raw material tank, is preformed to control the distillation column in a stationary state, and then a continuous treatment operation of the distillation apparatus is initiated; and an operational mode switching function in which an operational mode of the distillation apparatus is switched again to the circulation operation in the case where the liquid level in the raw material tank is lowered to a predetermined height during the continuous treatment operation or in the case where the liquid level in the product tank is raised to a predetermined height during the continuous treatment operation.

4. The apparatus of claim 1, wherein the distillation column further comprises a packing layer formed in the mid-stage portion.

5. The apparatus of claim 4, wherein the mid-stage portion comprises a thermometer.

6. The apparatus of claim 1, wherein a vertical section of the mid-stage portion of the distillation column comprises a weir configured to store the high-concentration NMP in a liquid state.

7. The apparatus of claim 6, wherein the weir has an annular shape, radially intersecting a height of the distillation column.

8. The apparatus of claim 7, wherein the weir comprises a common outer wall with an outer wall of the distillation column.

9. The apparatus of claim 7, wherein the weir comprises an internal vertical wall in a radially more central portion of the distillation column from an outer wall of the distillation column.

10. The apparatus of claim 9, wherein the liquid guard cover is arranged at least partially planar parallel to the weir and vertically over the weir.

11. The apparatus of claim 9, wherein the distillation column further comprises a distributor configured to feed the high-concentration NMP retained by the weir as a refluxed liquid to the bottom portion of the distillation column.

12. The apparatus of claim 7, wherein the weir comprises a common outer wall with an outer wall of the distillation column, and wherein the weir comprises an internal vertical wall in a radially more central portion of the distillation column from the outer wall.

13. The apparatus of claim 12, wherein the liquid guard cover is arranged at least partially planar parallel to the weir and vertically over the weir.

14. The apparatus of claim 13, wherein the distillation column further comprises a distributor configured to feed the high-concentration NMP retained by the weir as a refluxed liquid to the bottom portion of the distillation column.

15. A lithium ion battery electrode manufacturing facility, comprising the apparatus of claim 14.

16. The apparatus of claim 12, wherein the distillation column further comprises a distributor configured to feed the high-concentration NMP retained by the weir as a refluxed liquid to the bottom portion of the distillation column.

17. A lithium ion battery electrode manufacturing facility, comprising the apparatus of claim 12.

18. The apparatus of claim 6, wherein the distillation column further comprises a distributor configured to feed the high-concentration NMP retained by the weir as a refluxed liquid to the bottom portion of the distillation column.

19. The apparatus of claim 7, wherein the liquid guard cover is arranged at least partially planar parallel to the weir and vertically over the weir.

20. A lithium ion battery electrode manufacturing facility, comprising the apparatus of claim 1.

* * * * *